United States Patent

Kuriyama et al.

[11] Patent Number: 5,986,134
[45] Date of Patent: *Nov. 16, 1999

[54] PROCESSES FOR PRODUCING KETAZINE AND HYDRAZINE

[75] Inventors: Yasuhisa Kuriyama; Nobuhiro Nagata; Kiyoshi Yoshida, all of Yokkaichi, Japan

[73] Assignee: Mitsubishi Gas Chemical Company, Inc., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/684,403

[22] Filed: Jul. 19, 1996

[30] Foreign Application Priority Data

Aug. 14, 1995 [JP] Japan ................................ 7-207069

[51] Int. Cl.⁶ .................. C07C 241/00; C07C 241/02; C01B 21/16; C07B 249/16
[52] U.S. Cl. ............................................. 564/249; 423/407
[58] Field of Search ............................. 564/249; 423/407

[56] References Cited

U.S. PATENT DOCUMENTS

| | | | |
|---|---|---|---|
| 3,415,882 | 12/1968 | Jenkins et al. | 564/249 |
| 3,933,910 | 1/1976 | Waldmann et al. | 564/249 X |
| 3,943,152 | 3/1976 | Tellier et al. | 564/249 X |
| 3,948,902 | 4/1976 | Schirmann et al. | 564/249 |
| 3,951,964 | 4/1976 | Tellier et al. | 564/249 X |
| 3,956,282 | 5/1976 | Tellier et al. | 564/249 X |
| 3,959,262 | 5/1976 | Mathais et al. | 564/249 |
| 3,972,878 | 8/1976 | Schirmann et al. | 564/249 X |
| 4,005,179 | 1/1977 | Eichenhofer et al. | 423/407 |
| 4,093,656 | 6/1978 | Schirmann et al. | 564/249 |
| 4,233,242 | 11/1980 | Nagato et al. | 564/249 |
| 5,239,119 | 8/1993 | Schirmann et al. | 564/249 |
| 5,252,309 | 10/1993 | Krempf et al. | 423/407 |

FOREIGN PATENT DOCUMENTS

| | | | |
|---|---|---|---|
| 55766/90 | 11/1990 | Australia . | |
| 0070155 | 1/1983 | European Pat. Off. | 564/249 |
| 0399866 | 11/1990 | European Pat. Off. . | |
| 58-77853 | 5/1983 | Japan | 564/249 |
| 60-172956 | 9/1985 | Japan | 564/249 |
| 1004358 | 3/1983 | U.S.S.R. . | |
| 1446279 | 8/1976 | United Kingdom . | |

OTHER PUBLICATIONS

Patent Abstracts of Japan, vol. 095, No. 008, Sep. 29, 1995 of JP 07 126236 A, May 16, 1995 (abstract).
"Kirk–Othmer", Encyclopedia of Chemical Technology, 3rd Edition, vol. 12, 1980, pp. 734–755.

*Primary Examiner*—Floyd D. Higel
*Attorney, Agent, or Firm*—Frishauf, Holtz, Goodman, Langer & Chick, P.C.

[57] ABSTRACT

A process for continuously and stably synthesizing a ketazine from hydrogen peroxide, ammonia and methyl ethyl ketone in the presence of a solution containing a catalyst. The process comprises removing sec-butyl alcohol by distillation from methyl ethyl ketone, which is reused by circulation. Also a process for preparing a hydrazine hydrate which comprises hydrolyzing the ketazine. By circulating unreacted ketone, accumulation of impurities in the circulated ketone can be prevented to obtain a high yield of the ketazine and the hydrazine hydrate, for a long period of time.

11 Claims, No Drawings

PROCESSES FOR PRODUCING KETAZINE AND HYDRAZINE

BACKGROUND OF THE INVENTION

1. Field of the Invention

The present invention relates to a synthetic process for producing a ketazine, and more specifically, it relates to an industrial preparation process for producing a ketazine and a synthetic process for producing a hydrazine hydrate from the obtained ketazine. Incidentally, this ketazine is useful as an intermediate material from which the hydrazine hydrate is usually prepared.

2. Description of the Related Arts

Heretofore, as a preparation process of a hydrazine hydrate, there has been a process which comprises oxidizing ammonia with an oxidizing agent such as sodium hypochlorite or hydrogen peroxide in the presence of a ketone to synthesize a ketazine, and then hydrolyzing this ketazine.

In "Kirk-Othmer", 3rd Edition, Vol. 12, p. 734–755, there has been described a process for preparing a ketazine from hydrogen peroxide, ammonia and a ketone in the presence of an aqueous solution containing acetamide and sodium phosphate as shown by the chemical equation $$2NH_3 + 2R_1R_2C=O + H_2O_2 \rightarrow R_1R_2C=N-N=CR_1R_2 + 4H_2O.$$

In this process, the unreacted ketone present in the reaction mixture containing the ketazine can be collected therefrom and then reused. In this case, however, impurities produced during the synthetic reaction of the ketazine are collected together with the ketone, and the ketone containing the impurities is then reused by circulation, so that the impurities are accumulated in the circulated ketone, with the result that a reaction yield deteriorates.

SUMMARY OF THE INVENTION

The present invention has been developed in order to solve the above-mentioned problems, and an object of the present invention is to provide an industrially simple and economically advantageous process for continuously and stably preparing a ketazine. Another object of the present invention is to provide a process for efficiently preparing a hydrazine hydrate from the ketazine obtained herein.

Concretely, the present invention has a conception that while the unreacted ketone is circulated, the accumulation of impurities in the circulated ketone is prevented to maintain the yield of the ketazine in a ketazine synthetic reaction at a high level for a long period of time.

The present inventors have intensively investigated to solve the above-mentioned problems, and as a result, it has been found that in the ketazine synthetic reaction, the accumulation of sec-butyl alcohol produced from methyl ethyl ketone deteriorates a reaction yield. The present invention has been completed on the basis of this found knowledge.

That is to say, the present invention is directed to a synthetic process of a ketazine from hydrogen peroxide, ammonia and methyl ethyl ketone in the presence for producing a working solution containing a catalyst, said process comprising a step of removing sec-butyl alcohol by distillation from methyl ethyl ketone which is reused by circulation.

Furthermore, the present invention is directed to a synthetic process for producing a hydrazine hydrate which comprises the step of hydrolyzing the ketazine obtained by the above-mentioned process.

DESCRIPTION OF THE PREFERRED EMBODIMENTS

A synthetic process for producing a ketazine according to the present invention is a technique which comprises reacting hydrogen peroxide, ammonia and methyl ethyl ketone as materials in the presence of a working solution containing a catalyst, and in this case, various reaction procedures can be utilized. Above all, a preferable reaction procedure comprises the following steps (a) to (d). That is to say, (a) a synthetic step for producing the ketazine which comprises reacting ammonia, hydrogen peroxide and methyl ethyl ketone in the presence of a working solution containing a catalyst, (b) a step of separating the resulting mixture into a ketazine layer and a working solution layer, (c) a step of removing unreacted methyl ethyl ketone from the ketazine layer, and (d) a step of removing impurities (particularly sec-butyl alcohol) from unreacted methyl ethyl ketone, and then returning methyl ethyl ketone to the synthetic step for producing the ketazine.

In the above-mentioned step (a), as hydrogen peroxide which can be used as a reactant, various compounds can be used, but a 30 to 90% by weight aqueous $H_2O_2$ solution which is commercially available can usually be used.

Furthermore, as ammonia, gaseous ammonia or an aqueous ammonia solution can be used.

As methyl ethyl ketone, a commercially available product may be used at the first reaction, but afterward, unreacted methyl ethyl ketone after the synthetic reaction of the ketazine or a ketone produced at the hydrolysis of the ketazine can be collected and then reused. Alternatively, the circulated ketone can be used together with the commercially available product. This commercially available methyl ethyl ketone and the circulated methyl ethyl ketone may contain various impurities, but a ratio of secbutyl alcohol to methyl ethyl ketone which is used in the synthetic reaction of the ketazine is preferably 0.05 mol/mol or less, more preferably 0.03 mol/mol or less. If the concentration of sec-butyl alcohol in the methyl ethyl ketone to be used is more than 0.05 mol/mol, the yield of the ketazine in the synthetic reaction tend to deteriorate.

As the catalyst, an organic or an inorganic amide, an ammonium salt, an arsenic compound or a nitrile is preferable. Examples of the preferable amide include formamide, acetamide, monochloroacetamide and propionamide. Examples of the preferable ammonium salt include formates, acetates, monochloroacetates and propionates. Examples of the preferable arsenic compound include methylarsonic acid, phenylarsonic acid and cacodylic acid. Examples of the preferable nitrile include acetonitrile and propionitrile.

The working solution containing the catalyst can be prepared by dissolving or dispersing (suspending) this catalyst in water, an alcohol or a mixture thereof. In other words, this working solution can take any morphology of an aqueous solution, an alcohol solution, a mixed solution of water and the alcohol, a dispersion and a suspension thereof. In this case, examples of the alcohol include methanol, ethanol, ethylene glycol, propylene glycol, 1,3-propanediol, 1,3-butanediol, 1,4-butanediol and 1,5-pentanenediol.

The respective reactants can be used in stoichiometric amounts, but in general, methyl ethyl ketone can be used in an amount of 0.2 to 5 mol, preferably 1.5 to 4 mol per mol of hydrogen peroxide, and ammonia can be used in an amount of 0.1 to 10 mol, preferably 1.5 to 4 mol per mol of hydrogen peroxide. The amount of the working solution may be suitably selected in compliance with its kind, but it is usually in the range of 0.1 to 1 kg per mol of hydrogen peroxide.

The contact of the reaction material containing hydrogen peroxide, ammonia and methyl ethyl ketone with the working solution containing the catalyst can be carried out in an optional manner. The working solution containing the catalyst preferably contains a solvent in which the respective reactants can uniformly or partially be dissolved. The above-mentioned reaction can be carried out in an extremely wide temperature range, but it is preferably done in the range of 30 to 70° C. Furthermore, this reaction can be accomplished under an optional pressure, but it is simpler to do the operation under atmospheric pressure. The respective reactants can be added simultaneously or separately to the working solution in an optional order. As a reaction device, a stirrer-mixer or a fluidized bed is preferable in which the respective reactants can successfully be brought into contact with the working solution.

The separation of the ketazine layer from the working solution layer in the step (b) can be carried out by a known optional technique, for example, a mixer-settler, a centrifugal separator or a combination thereof.

The treatment in the step (c) is an operation for separating unreacted methyl ethyl ketone and the like from the ketazine layer separated in the step (b). The separation of methyl ethyl ketone and the like can be carried out by a distillation operation. According to this distillation operation, methyl ethyl ketone and highly volatile impurities can be removed as a distillate from the ketazine.

The distillation operation in the step (c) is preferably carried out under atmospheric pressure or under reduced pressure. Furthermore, not only continuous distillation but also batch distillation is similarly possible in the present invention. A column top temperature of a distillation column is set to the boiling point of the ketazine or less, and there are selected a structure of the distillation column and operating conditions which permit obtaining the ketazine having the highest possible purity from the bottom of the distillation column. The ketazine from which methyl ethyl ketone and the like have been removed in the step (c) can be used to prepare a hydrazine hydrate via a hydrolysis step, a purification step and the like.

The treatment in the step (d) is an operation for separating the impurities from methyl ethyl ketone separated from the step (c). The separation of the impurities can be accomplished by the distillation operation.

The impurities removed by the distillation can include components whose volatility is equal to or less than that of methyl ethyl ketone and equal to or more than that of ketazine. Above all, sec-butyl alcohol produced by the reduction of the carbonyl group of methyl ethyl ketone is typical of these impurities, and the removal of secbutyl alcohol enables methyl ethyl ketone to be circulatively used without the deterioration of the yield of the ketazine synthetic reaction.

The distillation of the step (d) can be carried out under an optional pressure, but the operation under atmospheric pressure is simpler. Furthermore, not only continuous distillation, but also batch distillation is similarly possible in the present invention. A structure of the distillation column and operating conditions are such that methyl ethyl ketone or an azeotropic mixture of methyl ethyl ketone and water is obtained in the column top portion of the distillation column and the impurities including sec-butyl alcohol are formed on the bottom of the distillation column.

The operation in the step (d) is not always carried out for the total amount of methyl ethyl ketone coming from the step (c). That is to say, it is not always necessary to remove the total amount of sec-butyl alcohol. The throughput of methyl ethyl ketone depends upon the amount of sec-butyl alcohol in methyl ethyl ketone. In addition, the amount of sec-butyl alcohol in the methyl ethyl ketone depends upon the synthetic conditions of the ketazine and the amount of sec-butyl alcohol previously present in methyl ethyl ketone. Typically, in the case that the ketazine synthetic reaction is carried out by the use of circulated methyl ethyl ketone, the throughput of methyl ethyl ketone is such that a molar ratio of sec-butyl alcohol to methyl ethyl ketone fed to a reactor is preferably 0.05 or less, more preferably 0.03 or less.

The steps (c) and (d) can simultaneously be done in one distillation column. In the case of the continuous distillation, for example, methyl ethyl ketone and the like can be separated as a distillate, and the ketazine and the like can be separated as bottoms, and sec-butyl alcohol and the like can be separated from the middle steps of the distillation column as a side cut solution. Alternatively, in the case of the batch distillation, for example, methyl ethyl ketone and the like can be separated as a first fraction, and sec-butyl alcohol and the like can be separated as a second fraction, and the ketazine and the like can be separated as a residue.

According to the present invention, the ketazine can stably be synthesized on an industrial scale, while unreacted ketone is circulated, and the hydrazine hydrate can also efficiently be prepared from this ketazine.

Next, the present invention will be described in detail with respect to examples, but the scope of the present invention should not be limited to these examples.

COMPARATIVE EXAMPLE 1

In a 200 ml four-necked flask made of glass and equipped with a stirrer was placed 100 ml of a working solution comprising 10% by weight of cacodylic acid, 30% by weight of ammonium propionate and 60% by weight of water. Next, while the solution was maintained at 55° C. and an ammonia gas was continuously blown into the flask, 36.1 g (0.50 mol) of methyl ethyl ketone, 3.7 g (0.05 mol) of secbutyl alcohol and 11.3 g ($H_{2\ O2}$=0.20 mol) of a 60% aqueous hydrogen peroxide solution were simultaneously added over 1 hour, and afterward, reaction was then carried out for 2 hours. The reaction mixture was allowed to stand, thereby separating it into a ketazine layer and a working solution layer, and the amount of the ketazine in each layer was then determined. As a result, the yield of the ketazine to the amount of added hydrogen peroxide was 60%.

EXAMPLE 1

40.1 g of the ketazine layer obtained in Comparative Example 1 was placed on the bottom of a fractionating column made of glass, and distillation was then carried out under atmospheric pressure. In consequence, there were obtained 15.2 g of a first fraction comprising 95% by weight of methyl ethyl ketone, 4% by weight of sec-butyl alcohol and 1% by weight of water, 6.9 g of a second fraction comprising 43% by weight of sec-butyl alcohol, 25% by weight of methyl ethyl ketazine and 32% by weight of water, and 15.8 g of a residue comprising 96% by weight of methyl ethyl ketazine and 4% by weight of high-boiling impurities.

The same ketazine synthetic reaction as in Comparative Example 1 was carried out by the same procedure as in Comparative Example 1 except that 17.4 g of this first fraction (methyl ethyl ketone=0.23 mol and sec-butyl alcohol=0.01 mol), 14.5 g (0.25 mol) of methyl ethyl ketone and 11.3 g (0.20 mol) of a 60% aqueous hydrogen peroxide solution were simultaneously added. As a result, the yield of the ketazine was 84%.

COMPARATIVE EXAMPLE 2

In a 1500 ml reactor made of stainless steel (SUS304) and equipped with a stirrer was placed 500 ml of a working solution comprising 5% by weight of cacodylic acid, 30% by weight of ammonium acetate and 50% by weight of propylene glycol. Next, while the solution was maintained at 50° C. and an ammonia gas was continuously blown into the reactor, 303 g (4.2 mol) of methyl ethyl ketone, 89 g ($H_2O_2$=2.1 mol) of a 80% aqueous hydrogen peroxide solution were simultaneously added over 30 minutes, and afterward, reaction was then carried out for 4 hours. The reaction mixture was allowed to stand, thereby separating it into a ketazine layer and a working solution layer, and the amount of the ketazine in each layer was then determined. As a result, the ketazine was obtained in a yield of 85% to the amount of added hydrogen peroxide.

The separated ketazine layer was fed to the fifth tray from the column top portion of a glass Oldershow type distillation column (inner diameter=27 mm, 20 trays, hereinafter referred to as "first column"), and distillation was then carried out at 200 Torr so that the total of concentrations of methyl ethyl ketone and sec-butyl alcohol in bottoms might be less than 1% by weight, thereby obtaining a distillate containing methyl ethyl ketone as a main component.

To this distillate, methyl ethyl ketone was added so that the total of methyl ethyl ketone might be 4.2 mol, and the resulting mixture was used as one of the reaction materials to carry out the same ketazine synthetic reaction as mentioned above.

A cyclic operation containing the synthesis of the ketazine, the separation of the ketazine layer and the distillation/collection of the unreacted ketone just described was repeated. As a result, when the above-mentioned operation was repeated 30 times, the amount of circulated sec-butyl alcohol which would be fed to a batch of the ketazine synthetic reaction was 0.3 mol, and the ketazine yield was as low as 68%.

EXAMPLE 2

The same procedure as in Comparative Example 2 was repeated except that 10% by weight of the distillate containing methyl ethyl ketone as a main component obtained in the first column was fed to a glass distillation column (inner diameter=10 mm, height=200 mm, filled with porcelaneous Raschig rings, and hereinafter referred to as "second column"), and distillation was then carried out at a column top temperature of 90° C. or less under atmospheric pressure. Next, methyl ethyl ketone was added to the remaining distillate in the first column and the distillate in the second column so that the total amount of methyl ethyl ketone might be 4.2 mol, and these distillates were then fed to a ketazine synthetic reaction.

As a result, even when a cyclic operation was repeated 100 times, the amount of circulated sec-butyl alcohol which would be fed to a batch of the ketazine synthetic reaction was 0.1 mol, and therefore the deterioration of ketazine yield was not observed.

What is claimed is:
1. A process for producing a ketazine which comprises;
   (a) reacting ammonia, hydrogen peroxide and methyl ethyl ketone in the presence of a solution containing a catalyst selected from the group consisting of an organic amide, an inorganic amide, an ammonium salt, an arsenic compound and a nitrile,
   (b) separating the resulting mixture from step (a) into a ketazine layer and a solution layer,
   (c) removing unreacted methyl ethyl ketone from the ketazine layer, and
   (d) distilling the unreacted methyl ethyl ketone to remove sec-butyl alcohol, wherein the removal of the sec-butyl alcohol is such that the sec-butyl alcohol concentration is 0.05 mol or less per mol of the methyl ethyl ketone, and
   (e) then returning the methyl ethyl ketone to step (a).
2. The process for producing a ketazine according to claim 1, wherein the catalyst is at least one catalyst selected from the group consisting of ammonium formate, ammonium acetate, ammonium monochloroacetate, ammonium propionate, methylarsonic acid, phenylarsonic acid and cacodylic acid.
3. The process for producing a ketazine according to claim 1, wherein the hydrogen peroxide is a 30 to 90 weight % $H_2O_2$ solution.
4. The process for producing a ketazine according to claim 1, wherein the sec-butyl is in an amount of 0.03 mol/mol or less of the methyl ethyl ketone.
5. The process for producing a ketazine according to claim 1, wherein the catalyst is selected from the group consisting of formamide, acetamide, monochloroacetamide, propionamide, acetonitrile and propionitrile.
6. The process for producing a ketazine according to claim 1, wherein the methyl ethyl ketone is in an amount of 0.2 to 5 mol per mol of the hydrogen peroxide, the ammonia is in an amount of 0.1 to 10 mol, and the solution is in an amount of 0.1 to 1 kg per mole of the hydrogen peroxide.
7. The process for producing a ketazine according to claim 1, wherein the methyl ethyl ketone is in an amount of 1.5 to 4 mol per mol of the hydrogen peroxide, the ammonia is in an amount of 1.5 to 4 mol, and the solution is in an amount of 0.1 to 1 kg per mole of the hydrogen peroxide.
8. The process for producing a ketazine according to claim 5, wherein step (a) is carried out at a temperature of 30 to 70° C.
9. The process for producing a ketazine according to claim 6, wherein the solution further comprises an alcohol or a mixture of alcohol and water.
10. The process for producing a ketazine according to claim 7, wherein the alcohol is selected from the group consisting of methanol, ethanol, ethylene glycol, propylene glycol, 1,3-propanediol, 1,3-butanediol, 1,4-butanediol and 1,5-pentanediol.
11. The process for producing a ketazine according to claim 1, wherein the catalyst is at least one catalyst selected from the group consisting of methylarsonic acid, phenylarsonic acid and cacodylic acid.

* * * * *